(12) United States Patent
Merkel et al.

(10) Patent No.: US 8,426,656 B2
(45) Date of Patent: Apr. 23, 2013

(54) INTEGRATED PROCESS TO CO-PRODUCE TRANS-1-CHLORO-3,3,3-TRIFLUOROPROPENE AND TRANS-1,3,3,3-TETRAFLUOROPROPENE

(75) Inventors: Daniel C. Merkel, West Seneca, NY (US); Robert Johnson, Lancaster, NY (US); Hsueh Sung Tung, Getzville, NY (US); Haiyou Wang, Amherst, NY (US); Konstantin A. Pokrovski, Orchard Park, NY (US)

(73) Assignee: Honeywell International Inc., Morristown, NJ (US)

( * ) Notice: Subject to any disclaimer, the term of this patent is extended or adjusted under 35 U.S.C. 154(b) by 257 days.

(21) Appl. No.: 12/754,070

(22) Filed: Apr. 5, 2010

(65) Prior Publication Data

US 2011/0245549 A1    Oct. 6, 2011

(51) Int. Cl.
*C07C 19/08*    (2006.01)

(52) U.S. Cl.
USPC ........... 570/170; 570/156; 570/157; 570/166; 570/167; 570/169

(58) Field of Classification Search .................. None
See application file for complete search history.

(56) References Cited

U.S. PATENT DOCUMENTS

| | | |
|---|---|---|
| 5,710,352 A | 1/1998 | Tung |
| 6,235,951 B1 | 5/2001 | Sakyu |
| 6,844,475 B1 | 1/2005 | Tung et al. |
| 7,230,146 B2 * | 6/2007 | Merkel et al. ................. 570/155 |
| 7,485,760 B2 | 2/2009 | Wang et al. |
| 7,592,494 B2 | 9/2009 | Tung et al. |
| 2005/0020862 A1 * | 1/2005 | Tung et al. .................... 570/164 |
| 2007/0238908 A1 | 10/2007 | Merkel |
| 2009/0118554 A1 | 5/2009 | Rao et al. |
| 2009/0124837 A1 | 5/2009 | Mukhapadhyay et al. |
| 2009/0240090 A1 | 9/2009 | Merkel et al. |
| 2009/0270661 A1 * | 10/2009 | Wang et al. ................... 570/156 |

FOREIGN PATENT DOCUMENTS

| | | |
|---|---|---|
| EP | 729932 A1 * | 9/1996 |
| EP | 0939071 | 9/1999 |
| WO | 2010035748 | 4/2010 |

* cited by examiner

*Primary Examiner* — Sudhakar Katakam
(74) *Attorney, Agent, or Firm* — Bruce O. Bradford

(57) ABSTRACT

The disclosed integrated manufacturing process includes a combined liquid phase reaction and purification operation which directly produces trans-1-chloro-3,3,3-trifluoropropene and 3-chloro-1,1,1,3-tetrafluoropropane which is a precursor to the manufacture of trans-1,3,3,3-tetrafluoropropene. The mixture of co-products is easily separated by conventional distillation and 3-chloro-1,1,1,3-tetrafluoropropane is then dehydrochlorinated to produce trans-1,3,3,3-tetrafluoropropene by contacting in the liquid phase with a caustic solution or in the vapor phase using a dehydrochlorination catalyst.

23 Claims, 1 Drawing Sheet

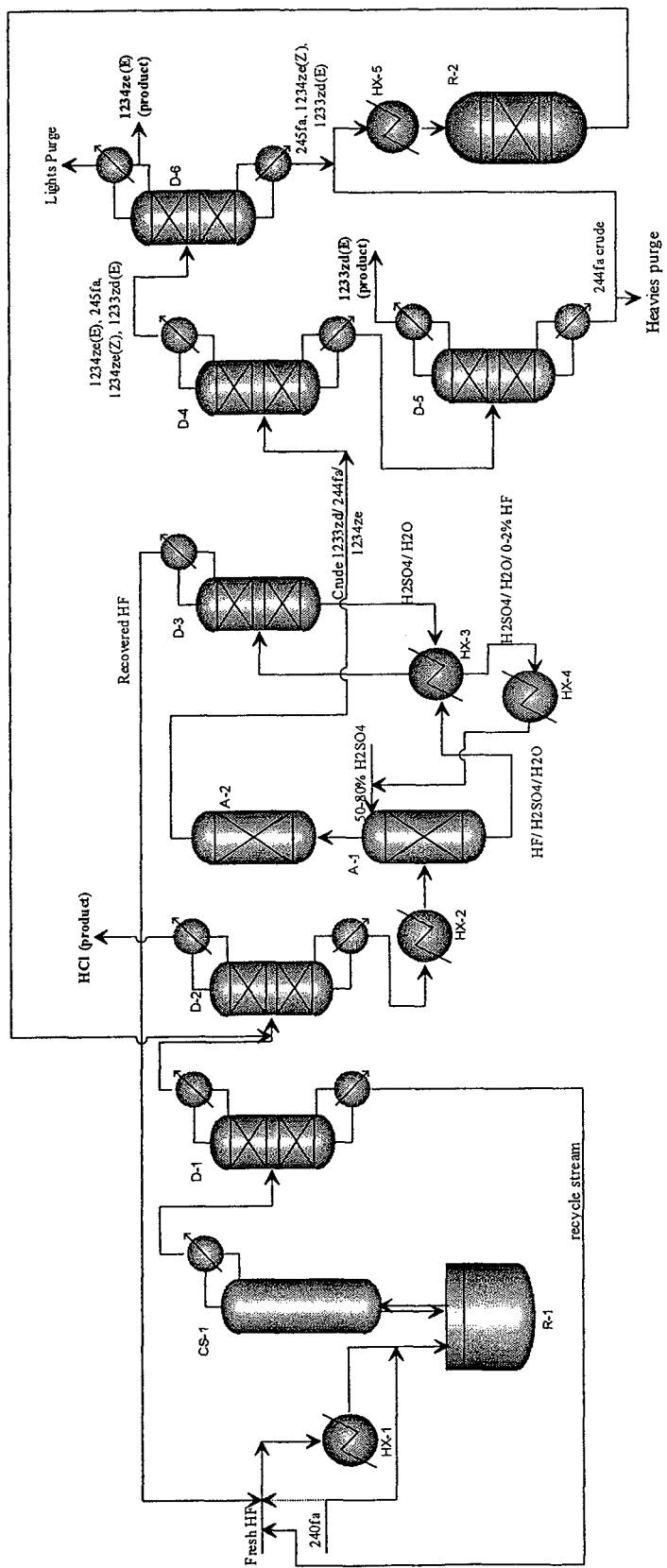

INTEGRATED PROCESS TO CO-PRODUCE TRANS-1-CHLORO-3,3,3-TRIFLUOROPROPENE AND TRANS-1,3,3,3-TETRAFLUOROPROPENE

FIELD OF THE INVENTION

A fully integrated process for co-manufacturing the compounds trans-1-chloro-3,3,3-trifluoropropene and trans-1,3,3-tetrafluoropropene is described.

BACKGROUND OF THE INVENTION

The use of chlorofluorocarbons or hydrochlorofluorocarbons as foam-blowing agents has been banned due to concerns that their release damages the ozone layer. More recently, foam-blowing (i.e., the addition of a volatile material to a polymeric mixture to cause a bubbled matrix which imparts insulation or cushioning value) has been accomplished through use of HFC-245fa; however, concern has been raised about the global warming potential (GWP) of this material.

One candidate to replace HFC-245fa as a foam-blowing agent is a liquid, trans-1-chloro-3,3,3-trifluoropropene, also known as HCFO-1233zd(E). This material also has potential use as a solvent, heat transfer composition, fire extinguishing/suppression composition, blowing agent, and compatabilizing agent. See, for example U.S. Pat. No. 6,844,475.

A second candidate for application as a single component foam-blowing agent is the gas, trans-1,3,3,3-tetrafluoropropene, also known as HFO-1234ze(E). See, for example, U.S. Pat. Nos. 7,230,146 and 7,485,760.

These two compounds represent the next generation of foam blowing agents. Several patents have been issued directed to processes for the production of these individual compounds, but the current invention discloses an integrated manufacturing process which economically co-produces both compounds starting from a single chlorinated hydrocarbon feed stock, namely 1,1,1,3,3-pentachloropropane (HCC-240fa).

The compounds of the present invention are part of a continued search for the next generation of low global warming potential materials. Such materials must have low environmental impact, as measured by low global warming potential and no substantial ozone depletion potential.

The preferred compounds of the present invention are environmentally acceptable and do not to contribute significantly the depletion of the earth's stratospheric ozone layer. The compounds and compositions of the present invention have no substantial ozone depletion potential (ODP), preferably an ODP of not greater than about 0.5 and even more preferably an ODP of not greater than about 0.25, most preferably an ODP of not greater than about 0.1; a global warming potential (GWP) of not greater than about 150, and even more preferably, a GWP of not greater than about 50.

As used herein, ODP is defined in the "Scientific Assessment of Ozone Depletion, 2002," a report of the World Meteorological association, incorporated here by reference.

As used herein, GWP is defined relative to that of carbon dioxide and over a 100 year time horizon, and defined in the same reference as for the ODP mentioned above.

SUMMARY OF THE INVENTION

It has been a recognized problem in the art to find economical processes for the formation of (E)-1-chloro-3,3,3-trifluoropropene (HCFO-1233zd(E)) and trans-1,3,3,3-tetrafluoropropene (HFO-1234ze(E)). It has now been found that these two compounds can be continuously and economically co-produced via an integrated manufacturing process which starts with a single chlorinated hydrocarbon, 1,1,1,3,3-pentachloropropane (HCC-240fa).

Thus, one embodiment of the present invention is a process for the formation of trans-1-chloro-3,3,3-trifluoropropene and trans-1,3,3,3-tetrafluoropropene comprising the steps of:

(a) reacting 1,1,1,3,3-pentachloropropane (HCC-240fa), 1,1,3,3-tetrachloropropene, or 1,1,1,3-tetrachloropropene, alone or in combination, with hydrogen fluoride in the presence of a fluorination catalyst to co-produce trans-1-chloro-3,3,3-trifluoropropene and 3-chloro-1,1,1,3-tetrafluoropropane; and (b) dehydrohalogenating the 3-chloro-1,1,1,3-tetrafluoropropane formed in step (a) to produce predominantly trans-1,3,3,3-tetrafluoropropene, predominately 1-chloro-3,3,3-trifluoropropene or a combination of both compounds (depending on the market need for the different compounds).

In certain embodiments the dehydrochlorination step takes place in the liquid phase by contact with a caustic solution. In other embodiments the dehydrochlorination step occurs in the vapor phase using a dehydrochlorination catalyst. In either case, the dehydrochlorination step further produces hydrogen chloride, which in the later case may be removed and purified.

Preferably, the fluorination reactions take place in a liquid phase reactor with excess hydrogen fluoride. In preferred embodiments the reactions are run using a relatively weak fluorination catalyst selected from the group consisting of $TiCl_4$, $SnCl_4$, $TaCl_5$, $SbCl_3$, $AlCl_3$, $SbCl_5$, and mixtures thereof. In certain embodiments the catalyst is partially fluorinated. In other embodiments, the catalyst is totally fluorinated.

Advantageously, the fluorination reactions are run under relatively non-corrosive conditions whereby a metal or alloy reactor can be used. In addition, the process of the present invention provides operational flexibility for producing different amounts of the desired compounds, simply by adjusting one or more of the following; operating conditions; concentrations of reactants; and catalyst employed in the first liquid phase reactor. Examples of these process controls are provided below.

Also advantageous, two products are produced from one capital investment which makes the cost less expensive. In addition, the ratio of the products can be adjusted to suit market conditions simply by varying the process conditions or selection of catalyst.

Another embodiment of the present invention is an integrated manufacturing process comprising combined liquid phase fluorination reaction and purification operations for the production of trans-1-chloro-3,3,3-trifluoropropene and 3-chloro-1,1,1,3-tetrafluoro-propane comprising the steps of:

(a) reacting 1,1,1,3,3-pentachloropropane (HCC-240fa), 1,1,3,3-tetrachloropropene, or 1,1,1,3-tetrachloropropene, alone or in combination, with anhydrous HF in excess in a liquid-phase catalyzed reactor, thereby producing trans-1-chloro-3,3,3-trifluoropropene and 3-chloro-1,1,1,3-tetrafluoropropane; and (b) separating the compounds produced in step (a).

In certain embodiments, this process further comprises the step of dehydrochlorinating the 3-chloro-1,1,1,3-tetrafluoropropane to produce trans-1,3,3,3-tetrafluoropropene. This step further produces hydrogen chloride which may be isolated and purified. In certain embodiments the dehydrochlorination step occurs in the liquid phase by contact with a caustic solution. In other embodiments the dehydrochlorination step occurs in the vapor phase using a dehydrochlorination catalyst.

Optionally, this process further comprises the step of dehydrofluorinating at least a portion of the 3-chloro-1,1,1,3-tetrafluoropropane to 1-chloro-3,3,3-trifluoropropene depending on product need. This step further produces hydrogen fluoride, which may be isolated and recycled back to the fluorination reactor.

BRIEF DESCRIPTION OF THE DRAWING

FIG. 1 shows a preferred arrangement of the processing apparatus used for the co-production of 1233zd(E) and 1234ze(E) according to the integrated process of this invention.

DETAILED DESCRIPTION OF THE INVENTION

As described above, trans-1-chloro-3,3,3-trifluoropropene (HCFO-1233zd(E)) and 3-chloro-1,1,1,3-tetrafluoropropane (HCFC-244fa) can be co-produced in the same liquid phase reactor using one hydrochloro-carbon feed. The reaction is run using a relatively weak fluorination catalyst and at conditions that are relatively non corrosive so that a metal or alloy reactor can be used. This provides a processing advantage over the known process to produce trans-1,3,3,3-tetrafluoropropene from a different precursor, 1,1,1,3,3-pentafluoropropane HFC-(245fa), which requires a fluoropolymer lined (e.g., Teflon®) reactor because the reagents are so corrosive. The known process also requires a larger quantity and a stronger fluorination catalyst.

There is an additional economical advantage to producing trans-1,3,3,3-tetrafluoropropene from HCFC-244fa precursor instead of HFC-245fa. They are both produced from the same hydrochlorocarbon, but 245fa has an extra fluoride ion ($F^-$) that was added to the original hydrochlorocarbon feed stock only to be removed as HF to produce trans-1,3,3,3-tetrafluoropropene. The fluoride ion ($F^-$) comes from HF and using HFC-245fa to produce trans-1,3,3,3-tetrafluoropropene wastes 1 mole of HF per mole of trans-1,3,3,3-tetrafluoropropene produced. On the other hand, trans-1,3,3,3-tetrafluoropropene is produced from HCFC-244fa by removing the last remaining chloride ion ($Cl^-$) (in the form of HCl) from the original hydrochlorocarbon feed stock. Thus, there is no waste, since the HCl can be recovered if desired.

The process of the present invention also has an advantage in that it allows for great flexibility in producing different amounts of each compound, simply by adjusting the operating conditions or concentrations of reactants and/or catalyst in the first liquid phase reactor.

The integrated manufacturing process of the present invention is different from known processes because it also includes the ability to recycle unreacted starting materials to maximize raw material utilization and product yields. It also provides the ability to isolate by-products, principally HCl, that may also be sold for commercial value.

Process Steps:

Overall the co-production process has two steps. The chemistry involves:

(1) The reaction of 1,1,1,3,3-pentachloropropane (HCC-240fa), 1,1,3,3-tetrachloropropene, or 1,1,1,3-tetrachloropropene, alone or in combination, with anhydrous HF in excess in a liquid-phase catalyzed reactor, which co-produces primarily trans-1-chloro-3,3,3-trifluoropropene and 3-chloro-1,1,1,3-tetrafluoropropane (plus byproduct HCl); and (2) The 3-chloro-1,1,1,3-tetrafluoropropane produced in step (1) is subsequently dehydrochlorinated to produce the desired second product trans-1,3,3,3-tetrafluoropropene. Optionally, the 3-chloro-1,1,1,3-tetrafluoropropane produced in step (1) can be subsequently dehydrohalogenated to produce the desired second product trans-1,3,3,3-tetrafluoropropene and the desired first product trans-1-chloro-3,3,3-trifluoropropene.

Step 1
Desired Reactions:

$$CCl_3CH_2CHCl_2 + 3HF \longrightarrow CF_3CH=CHCl + 4HCl$$
$$240fa \qquad\qquad\qquad\qquad 1233zd(E)$$
$$CCl_3CHC=HCl + 3HF \longrightarrow CF_3CH=CHCl + 3HCl$$
$$HCO\text{-}1230\text{ isomer} \qquad\qquad 1233zd(E)$$
$$CCl_2CH=CCl_2 + 3HF \longrightarrow CF_3CH=CHCl + 3HCl$$
$$HCO\text{-}1230\text{ isomer} \qquad\qquad 1233zd(E)$$
$$CF_3CH=CHCl + HF \longrightarrow CF_3CH_2CHFCl$$
$$(E\text{ or }Z)1233zd \qquad\qquad 244fa$$

Step 2
Desired Reaction(s):

$$CF_3CH_2CHFCl \longrightarrow CF_3CH=CHF + HCl$$
$$244fa \qquad\qquad 1234ze(E)$$

Optionally:

$$CF_3CH_2CHFCl \longrightarrow CF_3CH=CHF + CF_3CH=CHCl +$$
$$244fa \qquad\qquad 1234ze(E) \qquad 1233zd(E)$$
$$\qquad\qquad\qquad\qquad\qquad HF + HCl$$

Process Description

The manufacturing process consists of the following seven major unit operations.

The relative positions of these operations are shown in FIG. 1.

(1) Liquid phase fluorination catalyst preparation (titanium tetrachloride);

(2) Fluorination reaction (continuous or semi-batch mode) using HF with simultaneous removal of byproduct HCl and the co-products 1233zd(E) and 244fa;

(3) Separation and purification of byproduct HCl;

(4) Separation of excess HF back to (2);

(5) Purification of final product, 1233zd(E);

(6) Dehydrochlorination of 244fa to 1234ze(E) (with byproduct HCl can be recovered in (3); and (7) Purification of final product, 1233zd(E).

Liquid Phase Fluorination Catalyst Preparation

The reaction uses a liquid phase catalyst of proper strength to achieve the desired reaction preferentially. The present applicants have found that a catalyst comprised of titanium tetrachloride (liquid under ambient conditions) which has been partially or totally fluorinated by the action of anhydrous HF, achieves the desired degree of conversion without forming undesired volatile byproducts.

The catalyst fluorination is conducted by adding titanium tetrachloride to the agitated, temperature-controlled reactor vessel, and adding HF by a gradual flow. A moderate amount of HCl will be generated in the operation. The reaction conditions include a temperature in the range of from 10° to 50° C. and a pressure in the range of from about 0 to 100 psig.

Additional fluorination catalysts that can be used include (all may be partially or totally fluorinated by the action of anhydrous HF) $SnCl_4$, $TaCl_5$, $SbCl_3$, $AlCl_3$, $SbCl_5$, either alone or in combination.

Reaction and Stripping Column

One key to the process of the present invention is the equipment arrangement, which is illustrated in FIG. 1. An agitated, temperature-controlled reactor for the contact of both feed materials with the liquid catalyst and an integrated distillation column (operating in stripping mode) which permits the product to leave (along with byproduct HCl, traces of light organics [principally 1234ze(E+Z)], and sufficient anhydrous hydrogen fluoride (AHF) to form the azeotropes), while retaining the bulk of the HF, plus under-fluorinated and dimerized organics, plus the catalyst is key.

Preferably the reactor is constructed from materials which are resistant to the corrosive effects of the HF and catalyst, such as Hastelloy-C, Inconel, Monel, Incoloy, or fluoropolymer-lined steel vessels. Such liquid-phase fluorination reactors are well known in the art.

Once the catalyst has been prepared, the reaction can be initiated immediately. The flow of HF for the catalyst preparation need not be discontinued. An additional amount of HF is added to the reactor to fill the reactor to from about 20% to 90% of its volume while the reactor is heated to a temperature of from about 85° to 95° C. and agitated.

Next, the addition of the hydrochlorocarbon(s) (1,1,1,3,3-pentachloropropane (HCC-240fa), 1,1,3,3-tetrachloropropene, or 1,1,1,3-tetrachloropropene, alone or in combination) can be started immediately to cause continuous reaction while maintaining the flow of HF at an amount sufficient to produce the desired products plus an excess amount to account for losses due to azeotrope compositions of 1233zd (E)/HF and 244fa/HF that exit the top of the integrated distillation column. The reaction runs under HF rich conditions to produce the reaction co-products, 1233zd(E) and 244fa. Proper temperature control of the coolant (as discussed below) and sufficient reflux action are necessary for the stripping column to be effective.

General operating conditions which we have found to work well for the reaction and stripping are: Operating pressure of from about 80 to 140 psig maintained by a control valve on the exiting flow from the stripper column; reactor temperature of from about 85° to 115° C., primarily supplied by steam flow into the reactor jacket; application of −40 to 30° C. brine cooling to the heat exchanger on top of the stripper column to induce reflux; temperature in the center portion of the stripper column should range from about 10° to 40° C. below that in the reactor; additional heat input by superheating the HF vapor feed with high-pressure steam to from about 120° to 150° C.; feed rate of HF to maintain reactor and stripper conditions.

Removal of HCl

The HCl formed continuously during the reaction is removed from the reactor due to its volatile nature, and flows through the attached distillation column without condensing. The material can then be purified and collected for sale (or further purification) by using a low-temperature HCl distillation column. High purity HCl is isolated and can be absorbed in de-ionized water as concentrated HCl for sale.

Separation and Recycle of Excess HF Back to (2)

The overhead stream from the reactor stripper column (2) that contains crude product mixture of 1233zd(E) and about 30 wt % HF is fed to a sulfuric extractor or a phase separator for removal of HF from this mixture. HF is either dissolved in the sulfuric acid or phase separated from the organic mixture. HF is desorbed from the sulfuric acid/HF mixture by stripping distillation and recycled back to the reactor. The organic mixture either from the overhead of the sulfuric acid extractor may require treatment (scrubbing or adsorption) to remove traces of HF before it is fed to the next unit operation (5).

Purification of Final Product 1233zd(E)

Purification of final product 1233zd(E) consists of two continuously operating distillation columns. The first column is used to remove light ends from the 1233zd(E) and the second column is used to remove the heavier components, primarily 244fa, which is reacted further in (6). It should be recognized that at some point a purge of heavy byproducts from this stream will also be required.

Dehydrochlorination of HCFC-244fa to HFO-1234ze(E)

The bottoms stream from the second column in (5) is fed to a catalyzed vapor phase reactor where the HCFC-244fa is dehydrochlorinated to produce the desired HFO-1234ze(E) product and HCl. HFC-245fa from (7) will also react to form the desired product by dehydrofluorination. The reactor effluent is recycled back to the HCl recovery column (3).

Purification of Final Product HFO-1234ze(E)

Purification of final product HFO-1234ze(E) consists of a continuously operating distillation column. The feed stream is actually the light ends from the first distillation column in (5). The HFO-1234ze(E) is recovered as the distillate and the heavier components, primarily HFC-245fa, HFO-1234ze(Z), and HCFO-1233zd(E) exit the bottom and are co-fed into reactor (6). It should be recognized that at some point a purge of lights byproducts from the top of the column may also be required.

Processing System—See FIG. 1

Liquid phase reactor R1 is first charged with fluorination catalyst alone or in combination from the group comprising $TiCl_4$, $SnCl_4$, $TaCl_5$, $SbCl_3$, $AlCl_3$, or $SbCl_5$, alone or in combination. $TiCl_4$ is the most preferred catalyst. HF is first added in an amount to totally fluorinate the metal chloride catalyst; e.g., when using $TiCl_4$ a greater than 4:1 mole ratio of HF to catalyst is added. The catalyst preparation is done while the reactor is at a temperature of from about 10° to 50° C. and at a pressure of from about 0 to 160 psig. HCl is generated during catalyst preparation and can be vented out of the top of the catalyst stripper column CS-1 to control the reactor pressure at or below the intended operating pressure of the reactor.

Preferably the reactor is constructed from materials which are resistant to the corrosive effects of the HF and catalyst, such as Hastelloy-C, Inconel, Monel, Incoloy, or fluoropolymer-lined steel vessels. Such liquid-phase fluorination reactors are well known in the art.

Then additional HF is continuously added into R-1 via vaporizer, HX-1, until good agitation is achieved; this feed can be left on.

The reactor contents are then heated to about 85° C. with agitation at which point the HCC-240fa, 1,1,3,3-tetrachloropropene, or 1,1,1,3-tetrachloropropene, alone or in combination, feed is started and the fluorination reaction between the hydrochlorocarbon(s) and HF is initiated. A continuous stream of HCC-240fa, 1,1,3,3-tetrachloropropene, or 1,1,1,3-tetrachloropropene, alone or in combination is fed directly into reactor R-1 and not through heater HX-1. Optionally, hydrochlorocarbon(s) is fed to reactor R-1 via HX-1.

The operating pressure of from 60 to 160 psig, preferably from 80 to 140 psig, is maintained by a control valve on the exiting flow from the catalyst stripper column CS-1 and the reactor temperature is kept in the range of from about 80° to 150° C., preferably 85° to 115° C., primarily supplied by steam flow into the reactor jacket. A catalyst stripper column CS-1 is connected to the reactor, R-1, and serves the purpose of knocking down and returning entrained catalyst, some HF, partially fluorinated intermediates, and some unreacted hydrochlorocarbon feed stock back to the reactor for further reaction.

By adjusting the operating conditions or concentrations of reactants and/or catalyst in the liquid phase fluorination the reaction can be made to produce different amounts of each desired co-product.

The stream exiting the top of catalyst stripper CS-1 consisting of unreacted HCC-240fa, partially fluorinated intermediates and by-products, overfluorinated by-products, HF, HCFO-1233zd(E+Z), HCFC-244fa, and HCl, then enters recycle column D-1 where a stream consisting of mainly unreacted hydrochlorocarbon feed stock, partially fluorinated intermediates, and the majority of the HF exits the bottom of the recycle column and is recycled back to the liquid phase fluorination reactor R-1 via vaporizer HX-1.

A stream consisting of mainly HCFO-1233zd(E), HCFC-244fa, HF, and HCl exits the top of the recycle column D1 and enters HCl column D-2. A stream consisting of mainly HCl by-product exits the top of the HCl column and is fed to an HCl recovery system. The recovered HCl by-product can be sold for profit. The HCl column bottoms consisting mainly of HF, HCFO-1233zd(E), and HCFC-244fa are then fed into an HF recovery system. The HF recovery system starts with the crude HCFO-1233zd/HCFC-244fa/HF stream being vaporized in heat exchanger HX-2 and fed into HF absorption column A-1. Here a liquid stream of from 50 to 80% $H_2SO_4$ contacts the gaseous 1233zd/HF stream and absorbs the majority of the HF.

The stream exiting the bottom of A-1 consists of $HF/H_2SO_4/H_2O$ and is fed to heat exchanger HX-3 where it is heated to a temperature sufficient to flash the majority of the HF along with small amounts of $H_2O$ and $H_2SO_4$. This stream is fed to HF recovery distillation column D-3. The liquid remaining after the HF is flashed off in HX-3 consisting mainly of $H_2SO_4$ and $H_2O$ (with from 0 to 2% HF) is cooled in HX-4 and recycled back to HF absorption column A-1. The HF recovery column, D-3, bottoms stream consisting of mainly $H_2SO_4$ and $H_2O$ are recycled back to heat exchanger HX-3.

Anhydrous HF is recovered from the top of the HF recovery column, D-3, and is recycled back to the reactor R-1 via vaporizer are HX-1. The stream exiting the top of HF absorption column A-1 consisting of mainly HCFO-1233zd(E) and HCFC-244fa (trace HF) is sent forward to a polishing system A-2 where the gaseous stream contacts a water or a caustic solution to remove trace HF and is subsequently dried with a desiccant. Acid free crude product exiting absorber A-2 is sent to the first of three purification columns, D-4.

A stream exiting the top of the column D-4 consists mainly of HFO-1234ze(E) and reaction bi-products that have boiling points lower than that of HCFO-1233zd(E) is fed to HFO-1234ze(E) product recovery distillation column D-6. Product grade HFO-1234ze(E) exits the top of distillation column D-6 to product storage. The HFO-1234ze(E) product column bottoms consist mainly of HFC-245fa, HFO-1234ze(Z), and HCFO-1233zd(E). This bottoms stream after combination with the bottoms stream from 1233zd(E) product recovery column D-5 is fed to vaporizer HX-5 and then to vapor phase dehydrochlorination reactor R-2. The HFC-245fa impurity will to some extent dehydrofluorinate in R-2 to produce the desired HFO-1234ze(E) product.

The stream exiting the bottom of column D-4 consisting mainly of HCFO-1233zd(E+Z), 244fa and heavier bi-products is fed to HCFO-1233zd(E) product recovery distillation column D-5. Product grade HCFO-1233zd(E) exits the top of distillation column D-5 to product storage. The HCFO-1233zd(E) product column bottoms consist mainly of HCFC-244fa, HCFO-1233zd(Z) and reaction bi-products with boiling points higher than that of HCFO-1233zd(E). This bottoms stream after combination with the bottoms stream from HFO-1234ze(E) product recovery column D-6 is fed to vaporizer HX-5 and then to vapor phase dehydrochlorination reactor R-2. The HCFO-1233zd(Z) impurity will to some extent isomerize in R-2 to produce the desired HCFO-1233zd(E) product.

The vapor phase dehydrochlorination catalysts employed in R-2 may be metal halides, halogenated metal oxides, neutral (or zero oxidation state) metal or metal alloy, or activated carbon in bulk or supported form. When metal halides or metal oxides catalysts are used, they are preferably mono-, bi-valent metal halides, oxides and their mixtures/combinations.

Optionally, depending on the desired product mix a less selective dehydrochlorination catalyst may be used in R-2 that would partially produce 1233zd(E) product via dehydrofluorination of 244fa. These also include metal halides and halogenated metal oxides preferably tri-valent metal halides, oxides and their mixtures/combinations.

Component metals include, but are not limited to, $Cr^{3+}$, $Al^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Br^-$, and $I^-$. Examples of useful mono- or bi-valent metal halides include, but are not limited to, LiF, NaF, KF, CsF, $MgF_2$, $CaF_2$, LiCl, NaCl, KCl, and CsCl. Examples of useful tri-valent metal halides and metal oxides include $Al_2O_3$, $AlCl_3$, $AlF_3$, $Fe_2O_3$, $Fe_3O_4$, $FeCl_3$, $FeF_3$, $Cr_2O_3$, $CrF_3$, $CrO_xF_{3-2x}$. The metal oxides and/or fluorides and/or chlorides can be fully or partially chlorinated and/or fluorinated before or during the reaction. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used, useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Nickel, Monel 400, Incoloy 825, Inconel 625, Inconel 600.

Preferred catalysts include activated carbon, stainless steel (e.g., SS 316), austenitic nickel-based alloys (e.g., Inconel 625), nickel, fluorinated 10% CsCl/MgO, and 10% CsCl/$MgF_2$. The reaction temperature is preferably from about 300° to 550° C. and the reaction pressure is preferably from about 0 to 150 psig.

The reactor effluent from R-2 is recycled back to HCl recovery distillation column, D-2 where the HCl is recovered.

Optionally, the combined streams exiting the bottom of distillation columns D-5 and D-6 can be fed into a liquid phase stirred reactor along with a caustic solution to dehydrohalogenate HCFC-244fa and HFC-245fa and produce both desired products 1234ze(E) and 1233zd(E) as some of the 244fa will dehydrochlorinate and some will dehydrofluorinate.

Example 1

This example illustrates the continuous reaction where HCC240fa is continuously fed into a charge of Titanium halide catalyst and HF.

A clean, empty 10-gallon jacketed, agitated reactor of Hastelloy C construction was prepared. This reactor is connected to a 2 inch diameter vertical, PTFE-lined pipe containing packing material (stripper), which is in turn connected to an overhead heat exchanger. The heat exchanger is supplied with −40° C. brine circulation on the shell side. Vapors exiting this stripper are processed through a scrubber, in which temperature-controlled dilute potassium hydroxide aqueous solution is circulated. Vapors exiting this stripper are collected in a weighed, chilled (−40° C.) cylinder, followed by a smaller cylinder in series chilled in a dry ice bath.

Initially about 1200 grams of $TiCl_4$ was added as a catalyst, followed immediately by 28 pounds of HF. The reactor contents were heated to about 85° C. while agitated and was at a pressure of 120 psig after formation of HCl after catalyst fluorination. The HF feed to the reactor was continued at a rate of 1.0 pound/hr after being vaporized through a steam heated exchanger. Then a continuous feed of HCC-240fa was started at 1.0 pound/hr. The reactor was kept at a temperature in the range of from about 85° to 87° C. and at a pressure of 120 psig. Samples of the organic portion of the reactor effluent exiting the top of the catalyst stripper column were analyzed using a GC. Results showed about a 55 GC area % of HCFC244fa and about 42 GC area % HCFO-1233zd(E). The reactor ran continuously for 56 hours at these conditions with very consistent results.

Example 2

This example illustrates the semi-batch reaction where HCC240fa is continuously fed into a charge of Titanium halide catalyst and HF.

The same reactor as in Example 1 was used. The reactor was charged with 2600 grams of fresh $TiCl_4$ catalyst.

The process (reaction of HCC-240+HF in the presence of $TiCl_4$ catalyst) was changed from a completely batch process to a semi-continuous process with the hopes of reducing the residence time of the G240 in the reactor and thereby reducing the formation of the over fluorinated species, 244fa. The reactor was initially charged with 50 pounds of HF followed by 13 pounds of G240 and the reactor temperature was slowly increased and reaction was observed at a temperature in the range of from about 80° to 85° C. The reaction was allowed to proceed for a couple of hours with the lighter components continuously being taken overhead of the catalyst stripper column to the scrubber and product collection in dry ice cold traps (DITs).

The HCC-240 feed was then started continuously and added into the vapor space of the reactor. The overhead take-off system was modified so that a constant amount of material was taken off the catstripper and the G240 feed rate was adjusted to match that rate. Several times during the production run the reactor was shutdown to add more HF and started up again as before.

The selectivity of the reaction for producing 1233zd was surprisingly low at 40 to 50%. The major by-product was the over fluorinated species 244fa (50-55%). Perhaps the mole ratio of catalyst to G240 was too high and adversely affected the selectivity.

Example 3

This Example is 244fa dehydrohalogenation over metal chloride catalysts.

In Example 3, a series of mono-, bi-, and tri-valent metal chlorides were used as dehydrohalogenation catalysts, in which 20 ml of catalyst was used. 244fa was passed over each catalyst at a rate of 12 g/h at a temperature of 350° C.

As shown in Table 1, all the mono- and bi-valent metal chloride catalysts provided a 1234ze(E+Z) selectivity higher than 80% and a 1233zd(E+Z) selectivity lower than 20%, indicating these catalysts are more active for 244fa dehydrochlorination than its dehydrofluorination.

In comparison, the mono-valent metal chloride catalysts are more selective to form 1234ze(E+Z) than bi-valent metal chloride ones. A 244fa conversion higher than 90% was achieved over the following catalysts: 10.0 wt % LiCl/C, 10.0 wt % KCl/C, and 10.0 wt % $MgCl_2$/C. On the other hand, the tri-valent iron chloride catalyst exhibited a 1234ze(E+Z) selectivity of about 9% and a 1233zd(E+Z) selectivity of about 61%, which suggests that this catalyst is more active for 244fa dehydrofluorination than its dehydrochlorination.

TABLE 1

244fa dehydrohalogenation over metal chloride catalysts at 350° C.

| | | Selectivity, % (E + Z = mixture of E and Z isomers) | | | |
|---|---|---|---|---|---|
| Catalyst | Conversion, % 244fa | 1234ze (E + Z) | 245fa | 1233zd (E + Z) | others |
| 10.0 wt % LiCl/C | 96.2 | 95.2 | 0.0 | 4.4 | 0.4 |
| 10.0 wt % KCl/C | 97.9 | 94.4 | 0.0 | 4.9 | 0.7 |
| 10.0 wt % $MgCl_2$/C | 99.3 | 92.9 | 0.0 | 6.7 | 0.4 |
| 10.0 wt % $NiCl_2$/C | 89.3 | 93.4 | 0.0 | 5.4 | 1.2 |
| 10.0 wt % $CuCl_2$/C | 28.5 | 83.8 | 0.0 | 13.0 | 3.2 |
| 10.0 wt % $ZnCl_2$/C | 29.4 | 80.8 | 1.0 | 17.0 | 1.2 |
| 10.0 wt % $FeCl_3$/C | 66.8 | 9.4 | 24.3 | 61.4 | 4.9 |

Example 4

This Example is 244fa dehydrohalogenation over alkaline metal chloride-doped $MgF_2$ catalysts.

In Example 4, a series of alkaline metal chloride-doped $MgF_2$ catalysts are used as dehydrohalogenation catalysts, in which 20 ml of catalyst is used. 244fa is passed over each catalyst at a rate of 12 g/h at a temperature of 350° C.

As shown in Table 2, all the alkaline metal chloride-doped $MgF_2$ catalysts provide a 1234ze(E+Z) selectivity higher than 90% and a 1233zd(E+Z) selectivity lower than 5%, indicating these catalysts are much more active for 244fa dehydrochlorination than for its dehydrofluorination.

TABLE 2

Reactivity of alkaline metal chloride-doped $MgF_2$ catalysts during 244fa dehydrohalogenation at 350° C.

| | | Selectivity, % (E + Z = mixture of E and Z isomers) | | | |
|---|---|---|---|---|---|
| Catalyst | Conversion, % 244fa | 1234ze (E + Z) | 245fa | 1233zd (E + Z) | others |
| 10 wt % LiCl/$MgF_2$ | 42.9 | 90.5 | 0.0 | 4.8 | 4.7 |
| 10 wt % KCl/$MgF_2$ | 47.1 | 95.8 | 0.0 | 0.7 | 3.5 |
| 10 wt % CsCl/$MgF_2$ | 51.4 | 97.0 | 0.0 | 0.2 | 2.8 |

Example 5

This example illustrates the recovery of anhydrous HF from a mixture of HF, HCFO-1233zd, and HCFC244fa according to certain preferred embodiments of the present invention.

A mixture consisting of about 30 wt. % HCFO-1233zd(E), 40 wt. % HCFC-244fa, and about 30 wt. % HF was vaporized and fed to the bottom of a packed column at a feed rate of about 2.9 pounds per hour for about 4 hours. A stream of about 80 wt. % sulfuric acid (80/20 $H_2SO_4/H_2O$) with about 2% HF dissolved therein was fed continuously to the top of the same packed column at a feed rate of about 5.6 pounds per hour during the same time frame. A gaseous stream exiting the top of the column comprises HCFO-1233zd(E) and HCFC244fa with less than 1.0 wt. % HF therein. The concentration of HF in the sulfuric acid in the column bottoms increases from 2.0 wt. % to about 15 wt. %.

The column bottoms containing sulfuric acid and about 15 wt. % HF was collected and charged into a 2 gallon Teflon® lined vessel. The mixture was heated to about 140° C. to vaporize and flash off HF product, which was collected. The collected HF product contained about 6000 ppm water and 500 ppm sulfur. The sulfuric acid contained about 500 ppm of TOC (total organic carbon).

The HF collected from flash distillation was distilled in a distillation column and anhydrous HF is recovered. The recovered anhydrous HF contained less than 50 ppm of sulfur impurities and less than 100 ppm water Example 6

This example demonstrates the purification of the acid free 1233zd(E) crude product via distillation column D-5 in FIG. 1.

92 pounds of acid free 1233zd/244fa crude material produced in Example 2 was charged to a batch distillation column. The crude material contained about 94 GC area % and 6 GC area % impurities. The distillation column consisted of a 10 gallon reboiler, 2 inch ID by 10 feet propack column and a shell and tube condenser. The column had about 30 theoretical plates. The distillation column was equipped with temperature, pressure, and differential pressure transmitters. About 7 pounds of a lights cut was recovered which consisted of mainly 1234ze(Z+E), trifluoropropyne, 245fa, and 1233zd (E). 82 pounds of 99.8+ GC area % 1233zd(E) were collected. The reboiler residue amounting to about 3 pounds was mainly 244fa, 1233zd(Z), 1233zd dimmer, and 1233zd(E). The recovery of 99.8+ GC area % pure 1233zd(E) was 94.8%.

Example 7

This example demonstrates the use of the recycle column D1 in FIG. 1.

A representative 1233zd(E).244fa liquid phase reactor effluent mixture as determined in Example 2 was charged into a batch distillation column. The distillation column consisted of a 10 gallon reboiler, 2 inch inner diameter by 10 feet (long) propack column, and a shell and tube condenser with −40° C.

coolant flow capability. The column had about 30 theoretical plates. The distillation column was equipped with temperature, pressure, and differential pressure transmitters. The distillation column feed mixture was about 30 wt % HF, 37 wt % HCl and 33% 1233zd(E)/244fa crude. The distillation was run at a pressure of about 100 psig and a differential pressure (delta P) of 15-20 inches of water. Both the distillate and reboiler are sampled periodically and analyzed for organic, HF, and HCl using gas and ion chromatography.

Initially, HCl, organic, and HF were observed in both samples. As more material was removed as distillate the concentration of the reboiler changes. First, the concentration of HCl decreased until it was undetectable. The distillation was allowed to proceed until the concentration of organic in the reboiler sample decreases to only trace amounts as analyzed using gas chromatography. At the conclusion of the distillation the material remaining in the reboiler was essentially pure HF. The recovered HF (reboiler bottoms) was then used to demonstrate recycle of recovered HF back to the liquid phase fluorination reactor and works satisfactorily.

Example 8

This example illustrates the continuous distillation of the crude mixture consisting essentially of HFO-1234ze(E), HFO-1234ze(Z), and HFC-245fa.

The distillation column consisted of a 10 gallon reboiler, 2 inch inner diameter by 10 foot (long) propack column, and a shell and tube condenser. The column had about 30 theoretical plates. The distillation column was equipped with reboiler level indicator; temperature, pressure, and differential pressure transmitters. The distillation was run at pressure of about 50 psig and differential pressure of about 17 inches of $H_2O$ in the continuous mode.

The feed consisting essentially of HFO-1234ze(E), HFO-1234ze(Z), HFC-245fa, and small amount of impurities (see Table 3) was continuously feed via the inlet port at the bottom of the distillation column at the rate of about 1.75 lb/hr. The distillate consisting essentially of HFO-1234ze(E) and light impurity (see Table 3) was collected from the top of the condenser at the rate of about 1.02 lb/hr. The stream consisting essentially of HFC-245fa and HFO-1234ze(Z) (see Table 3) was continuously taken out from the bottom of reboiler at the rate of about 0.73 lb/hr in order to maintain the level of material in the reboiler at about 40%. The distillation was run continuously for about 1000 hours.

TABLE 3

Composition of 1234ze(E) distillation column streams

| | 3,3,3-trifluoropropyne Wt. % | HFO-1234ze(E) Wt. % | HCFO-1234zc Wt. % | HFO-1234ze(Z) Wt. % | HCFO 1233zd Wt. % | HFC-245fa Wt. % |
|---|---|---|---|---|---|---|
| Feed composition | 0.0263 | 58.1003 | 0.0253 | 11.3939 | trace | 30.4542 |
| Distillate composition | 0.0497 | 99.9503 | 0.0000 | — | — | — |
| Bottoms composition | — | 0.0801 | 0.0604 | 27.1886 | trace | 72.6709 |

Examples 9 and 10

These Examples provide 244fa dehydrohalogenation to 1234ze(E+Z) and 1233zd(E+Z).

In Example 9, fluorinated $Cr_2O_3$ was used as a dehydrohalogenation catalyst, with 20 ml of catalyst charged into a ¾-inch diameter monel reactor. 244fa feed was passed through the catalyst at a rate of 12 grams/hour at a temperature of 350° C.

As shown in Table 4, the fluorinated $Cr_2O_3$ catalyst provided a 1233zd selectivity of about 75% and a 1234ze selectivity of about 21%, indicating 1234ze and 1233zd can be co-produced from 244fa dehydrohalogenation over this catalyst. All 244fa was converted during the reaction.

TABLE 4

244fa dehydrohalogenation over a fluorinated metal oxide catalyst at 350° C.

| | | Selectivity, % (E + Z = mixture of E and Z isomers) | | | |
|---|---|---|---|---|---|
| Catalyst | 244fa conv. (%) | 1234ze (E + Z) | 245fa | 1233zd (E + Z) | others |
| Fluorinated $Cr_2O_3$ | 100.0 | 20.7 | 0.0 | 74.6 | 4.7 |

In Example 10, aluminum fluoride was used as dehydrohalogenation catalyst. 20 ml of catalyst was charged into a ¾-inch diameter monel reactor. 244fa feed was passed through each catalyst at a rate of 12 grams/hour at a temperature of 350° C.

As shown in Table 5, the $AlF_3$ catalyst provided a 1233zd selectivity of about 77% and a 1234ze selectivity of about 22%, indicating 1234ze and 1233zd can be co-produced from 244fa dehydrohalogenation over this catalyst. All 244fa was converted during the reaction.

TABLE 5

244fa dehydrohalogenation over a metal halide catalyst at 350° C.

| | | Selectivity, % (E + Z = mixture of E and Z isomers) | | | |
|---|---|---|---|---|---|
| Catalyst | 244fa conv. (%) | 1234ze (E + Z) | 245fa | 1233zd (E + Z) | Others |
| $AlF_3$ | 100.0 | 21.8 | 0.0 | 77.3 | 0.9 |

Example 11

This Example demonstrates the dehydrohalogenation of HCFC244fa is a caustic solution to produce both 1234ze(E) and 1233zd(E).

539.5 grams of 9.3 wt % KOH solution and 135.4 grams of 90.0 GC area % pure 3-chloro-1,1,1,3-tetrafluoropropane (HCFC-244fa) were added to a 1.0 liter stainless steel cylinder. The other major component was HCFO-1223xd which amounted to 9.2 GC area %. The cylinder was heated to 75° to 80° C. and shaken for five (5) hours. A sample of the vapor space showed the presence of 75.6 area % HFO-1234ze trans isomer, 12.9 area % HFO-1234ze cis isomer, 8.5 GC area % HCFC-244fa, and 0.8 GC area % HCFO-1223xd. A sample of the organic liquid phase showed 24.4 GC area % HFO-1234ze(E), 12.9 GC area % HCFO-1233zd(E) isomer, 44.2 GC area % HCFC-244fa, and 8.1 GC area % HCFO-1223xd.

560.0 grams of aqueous solution was collected after the experiment which amounts to a weight gain of 20.5 grams in the aqueous layer. Assuming this weight gain was HCl that was produced during the dehydrochlorination of 244fa it was calculated that about a 60% conversion of HCFC-244fa to HFO-1234ze occurred during the reaction.

It should be understood that the foregoing description and examples are only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the formation of trans-1-chloro-3,3,3-trifluoropropene and trans-1,3,3,3-tetrafluoropropene comprising the steps of:
    (a) reacting 1,1,1,3,3-pentachloropropane, 1,1,3,3-tetrachloropropene, or 1,3,3,3-tetrachloropropene, alone or in combination, with hydrogen fluoride in the presence of a fluorination catalyst to co-produce greater than about 50% yield of trans-1-chloro-3,3,3-trifluoropropene and 3-chloro-1,1,1,3-tetrafluoropropane; and
    (b) dehydrohalogenating the 3-chloro-1,1,1,3-tetrafluoropropane formed in step (a) to produce greater than about 50% yield of trans-1,3,3,3-tetrafluoropropene and/or trans-1-chloro-3,3,3-trifluoropropene.

2. The process of claim 1, wherein dehydrohalogenation reaction is dehydrochlorination reaction.

3. The process of claim 1, wherein dehydrohalogenation reaction is dehydrofluorination reaction.

4. The process of claim 1, wherein the dehydrohalogenation reactions of step (b) take place in the liquid phase by contact with a caustic solution.

5. The process of claim 1, wherein the dehydrohalogenation reactions of step (b) occur in the vapor phase using a dehydrohalogenation catalyst.

6. The process of claim 1, wherein the dehydrohalogenation step (b) further produces hydrogen chloride and hydrogen fluoride.

7. The process of claim 1, wherein the dehydrohalogenation catalyst is selected from metal halides, halogenated metal oxides, neutral (or zero oxidation state) metals or metal alloys, or activated carbon in bulk or supported form or mixtures of thereof.

8. The process of claim 7, wherein the dehydrohalogenation catalyst is selected from mono-, bi-, or tri-valent metal oxides, halogenated metal oxides supported or bulk or mixtures of thereof.

9. The process of claim 7, wherein dehydrohalogenation catalyst is selected from the list of $CsCl/MgF_2$, $KCl/MgF_2$, $CsCl/MgO$, $KCl/MgO$, $CsCl/MgCl_2$, $KCl/MgCl_2$, $Al_2O_3$, $AlCl_3$, $FeCl_3$, $Cr_2O_3$, $CrO_xF_{3-2x}$.

10. The process of claim 1, wherein the reactions of step (a) take place in a liquid phase reactor with excess hydrogen fluoride.

11. The process of claim 10, wherein the reactions are run using a relatively weak fluorination catalyst selected from the group consisting of $TiCl_4$, $SnCl_4$, $TaCl_5$, $SbCl_3$, $AlCl_3$, $SbCl_5$, and mixtures thereof.

12. The process of claim of claim 11, wherein the catalyst is partially fluorinated.

13. The process of claim of claim 11, wherein the catalyst is totally fluorinated.

14. The process of claim 1, wherein the process allows for flexibility in producing different amounts of each compound, simply by adjusting one or more of the following; operating conditions; concentrations of reactants; and catalyst employed in the steps (a) and/or (b).

15. An integrated manufacturing process comprising combined liquid phase reaction and purification operation for the production of trans-1-chloro-3,3,3-trifluoropropene and 3-chloro-1,1,1,3-tetrafluoropropane comprising the steps of:

(a) reacting 1,1,1,3,3-pentachloropropane, 1,1,3,3-tetrachloropropene, or 1,3,3,3-tetrachloropropene, alone or in combination, with anhydrous HF in excess in a liquid-phase catalyzed reactor, thereby producing greater than about 50% yield of trans-1-chloro-3,3,3-trifluoropropene and 3-chloro-1,1,1,3-tetrafluoropropane; and (b) separating the compounds produced in step (a).

16. The process of claim 15, which further comprises the step of dehydrohalogenating the 3-chloro-1,1,1,3-tetrafluoropropane to produce trans-1,3,3,3-tetrafluoropropene and 1-chloro-3,3,3-trifluoropropene.

17. The process of claim 16, wherein the dehydrohalogenation step further produces hydrogen chloride and hydrogen fluoride.

18. The process of claim 17, wherein the dehydrohalogenation step occurs in the liquid phase by contact with a caustic solution.

19. The process of claim 17, wherein the dehydrohalogenation step occurs in the vapor phase using a dehydrohalogenation catalyst.

20. The process of claim 1, wherein at least 50% 3-chloro-1,1,1,3-tetrafluoropropane is formed in step (a).

21. The process of claim 1, wherein at least 40% trans-1-chloro-3,3,3-trifluoropropane is formed in step (a).

22. The process of claim 1, wherein at least 50% trans-1-chloro-3,3,3-trifluoropropene is formed in step (b).

23. The process of claim 1, wherein at least 50% trans-1,3,3,3-tetra-fluoropropene is formed in step (b).

* * * * *